(12) United States Patent
Strube et al.

(10) Patent No.: US 7,754,484 B2
(45) Date of Patent: Jul. 13, 2010

(54) USE OF ESTERS OF UNSATURATED, PHYSIOLOGICALLY ACTIVE FATTY ACIDS AS NUTRIENT MEDIA FOR CELL CULTURES

(75) Inventors: Albert Strube, Neuss (DE); Claudia Scholz, Berlin (DE); Jochen Seifert, Muehltal (DE); Christophe Carite, Rilhac-Rancon (FR); Christophe Sicre, Landorthe (FR); Valerie Eychenne, Toulouse (FR)

(73) Assignee: Cognis IP Management GmbH, Duesseldorf (DE)

( * ) Notice: Subject to any disclaimer, the term of this patent is extended or adjusted under 35 U.S.C. 154(b) by 665 days.

(21) Appl. No.: 11/595,538

(22) Filed: Nov. 10, 2006

(65) Prior Publication Data

US 2007/0231902 A1  Oct. 4, 2007

(30) Foreign Application Priority Data

Nov. 16, 2005 (DE) .................... 10 2005 054 577

(51) Int. Cl.
*C12N 5/02* (2006.01)
(52) U.S. Cl. .................... 435/383; 435/325; 435/404; 435/410; 435/431; 435/243
(58) Field of Classification Search ............... 435/325, 435/404, 383, 410, 431, 243
See application file for complete search history.

(56) References Cited

U.S. PATENT DOCUMENTS 4,762,792 A  8/1988  Girgis et al.
5,122,536 A * 6/1992  Perricone .................... 514/474
5,502,077 A  3/1996  Breivik et al.

FOREIGN PATENT DOCUMENTS

| DE | 39 26 658 C2 | 10/1998 |
| EP | 0 515 460 B1 | 4/1998 |
| WO | WO 9012083 A1 * | 1/1990 |
| WO | WO 9003429 A1 * | 4/1990 |
| WO | WO 98/03671 A1 | 1/1998 |
| WO | WO 9957246 A1 * | 11/1999 |

OTHER PUBLICATIONS

Cortesi et al. Pharma. Sci. Technol. Today (PSTT) (1999) 2(7): 288-298.*
Sigma Catalog (1998).*

* cited by examiner

*Primary Examiner*—Sandra Saucier
*Assistant Examiner*—Susan Hanley

(57) ABSTRACT

The disclosed invention relates to the use of esters of unsaturated, physiologically active fatty acids as nutrient media for cell cultivation and, more particularly, as a substitute for foetal bovine serum. In one aspect, the esters comprise more than 50 mol-% of physiologically active fatty acids containing 16 to 24 carbon atoms and 2 to 5 double bonds as the acid component and a lower $C_{1-4}$ alcohol, preferably ethanol, or a sterol as ester component. In another aspect, the esters comprise a transesterification product of natural or synthetic oils or a mixture of such oils having greater than 50 mol-% of unsaturated, physiologically active fatty acids, based on the acyl group, and a lower $C_{1-4}$ alcohol or a sterol. In a further aspect, the esters are used together with sterols, phospholipids and/or vegetable proteins or are liposomally encapsulated.

4 Claims, No Drawings

USE OF ESTERS OF UNSATURATED, PHYSIOLOGICALLY ACTIVE FATTY ACIDS AS NUTRIENT MEDIA FOR CELL CULTURES

CROSS-REFERENCE TO RELATED APPLICATIONS

This application claims priority under 35 U.S.C. §119 from German Patent Application No. 10 2005 054 577.7, filed Nov. 16, 2005.

BACKGROUND OF THE INVENTION

This invention relates generally to cell cultivation and, more particularly, to the use of special fatty acid lower alkyl esters as nutrient media for cell cultures and, more particularly, as a substitute for foetal bovine serum (FBS).

By virtue of its broad scope of application, foetal bovine serum is the serum most widely used for the in vitro cultivation of cells, tissues and organs both in industry and in medicine and science. Worldwide demand—which is covered almost exclusively by foetal calf serum—amounts to around 500,000 liters per year.

The blood from the animal foetuses used for FBS production is normally obtained by drilling through the umbilical cord or the jugular vein, although for septic reasons the heart is preferably punctured. Although the view widely held among experts is that the foetus dies at about the same time as the mother animal, it cannot be ruled out that the foetus may survive for some time after the time the heart of the mother animal has stopped beating because scientific studies have shown that foetuses and newborns are capable of managing lack of oxygen comparatively well. Nor can it be ruled out that the foetus feels pain which makes the process of obtaining FBS an ethically questionable practice.

Accordingly, the problem addressed by the present invention—in the context of sustainability and animal welfare—was to provide a nutrient medium for a large number of very different cell lines with sufficient solubility in the cultures which would be comparable in its properties with serum of animal origin, but which could be obtained synthetically, preferably using vegetable or marine starting materials, and which would therefore render the production of FBS superfluous in the medium term.

U.S. Pat. No. 4,762,792 discloses a water-based, animal lipoprotein concentrate.

BRIEF SUMMARY OF THE INVENTION

The present invention relates to the use of esters of unsaturated, physiologically active fatty acids as a nutrient medium for cell cultivation, more particularly as a substitute for foetal bovine serum.

In one aspect, the esters comprise more than 50 mol-% of physiologically active fatty acids containing 16 to 24 carbon atoms and 2 to 5 double bonds as the acid component and a lower $C_{1-4}$ alcohol, preferably ethanol, or a sterol as ester component. In another aspect, the esters comprise a transesterification product of natural or synthetic oils or a mixture of such oils having greater than 50 mol-% of unsaturated, physiologically active fatty acids, based on the acyl group, and a lower $C_{1-4}$ alcohol or a sterol.

In a further aspect, the esters are used together with sterols, phospholipids and/or vegetable proteins or are liposomally encapsulated.

DETAILED DESCRIPTION OF THE INVENTION

It has surprisingly been found that the esters to be used in accordance with the invention have excellent nutrient properties, as demonstrated, for example, in tests on cell lines of the "BHK type" (fibroblasts of hamster kidneys), the "Vero" type (fibroblasts of green monkey kidneys) or the "MRC 5" type (fibroblasts from human lung tissue), and are equivalent or even superior to FBS in this regard.

Unsaturated, Physiologically Active Fatty Acid Esters

A common criterion of the physiologically active fatty acid esters to be used in accordance with the invention is that they should have a sufficiently long lipid residue and a sufficient number of double bonds. Accordingly, esters of fatty acids containing 16 to 26 carbon atoms and 2 to 6 double bonds are particularly suitable for this purpose.

In a first embodiment of the invention, esters of conjugated linoleic acid (CLA), preferably those with lower aliphatic alcohols containing 1 to 4 carbon atoms and more preferably ethyl esters thereof, are used for this purpose. These esters are known substances which can be produced, for example, by base-catalyzed isomerization of thistle oil or corresponding alkyl esters, subsequent enzymatic hydrolysis and esterification. It has proved to be of advantage for the CLA component to meet a certain specification, according to which the acyl group contains at least 30% by weight t10,c12-isomers, at least 30% by weight c9,t11 isomers and, in all, less than 1% by weight 8,10-11,13- and t,t-isomers. Corresponding starting acids are marketed, for example, under the name of Tonalin® CLA-80 (Cognis).

In a second alternative embodiment, other suitable esters are esters of so-called omega fatty acids and particularly omega-3 fatty acids which typically contain 18 to 26 and more particularly 20 to 22 carbon atoms and at least 4 to 6 double bonds. These esters are also obtainable by standard methods of organic chemistry, for example by transesterification of fish oil, precipitation of the $C_{1-4}$ alkyl esters obtained with urea and subsequent extraction with nonpolar solvents, as described in German patent DE 3926658 C2 (Norsk Hydro). Mixtures of fatty acid esters rich in omega-3 (all-Z)-5,8,11,14,17-eicosapentaenoic acid (EPA) C20:5 and (all-z)-4,7,10,13,16,19-docosahexaenoic acid (DHA) C22:6 are obtained in this way. Starting fatty acids such as these are marketed, for example, under the name of Omacor® (Pronova). Alternatively, oils with an equally high EPA and DHA content can also be obtained by microbial techniques, namely by fermentation of certain fungi or microalgae, as described for example in EP 0515460 B1 (Martek) or WO 98/003671 A1 (Santory).

However, the physiologically active components may be used not only in the form of their lower alkyl esters, but also in the form of their esters with sterols. The sterol esters have the advantage that they are readily absorbed and are also readily cleaved under physiological conditions. In addition, another physiologically active component is released with the sterol. The terms "sterol", "stanol" and "sterin" are synonymous and denote steroids which have only a hydroxyl group at C-3, but no other functions. In addition, the sterols containing 27 to 30 carbon atoms may contain a double bond, preferably in the 5/6 position. Typical examples are the esters with β-sitosterol, campesterol, brassicasterol, avenasterol and stigmasterol. Preferred compounds for the purposes of the invention are the esters of CLA or omega fatty acids with β-sitosterol or its hydrogenation product, β-sitostanol.

In one preferred embodiment, transesterification products of a natural or synthetic oil or an oil mixture with a high content, preferably of more than 50 and, more particularly, more than 75 mol-%, of unsaturated, physiologically active fatty acids—based on the acyl groups—and a lower $C_{1-4}$ alcohol, preferably ethanol, or a sterol are used as the physiologically active components. The starting oils or oil mixtures are preferably of a vegetable, marine or microbial nature and may even be mixtures of such substances. Typical examples are thistle oil, sunflower oil, rapeseed oil, olive oil, linseed oil, cottonseed oil, rice oil, mackerel oil, sardine oil, herring oil and the microbial oils mentioned at the beginning from the fermentation of marine microorganisms. The transesterification of these oils may be carried out in known manner, i.e. optionally in the presence of an alkaline catalyst, without involving the expert in inventive activity.

In another preferred embodiment, the esters of the unsaturated, physiologically active fatty acids may be mixed with sterols. Here, too, typical examples of suitable sterols are campesterol, brassicasterol, avenasterol, stigmasterol and, more particularly, β-sitosterol. The mixing ratio may be from 99:1 to 50:50 and is preferably from 98:2 to 75:25 and more particularly from 95:5 to 90:10 parts by weight. Mixtures of CLA ethyl ester and β-sitosterol, more particularly in a ratio by weight of 99:1 to 96:4, are particularly preferred. The advantage of using these mixtures lies in the better cultivation results obtained with special cell lines, for example with epithelial cells of hamster ovaries (CHO).

In order to improve the solubility of the fatty acid esters to be used in accordance with the invention, it has proved to be of advantage to use phospholipids. To this end, the fatty acid esters may either be mixed with the phospholipids, which preferably have the same acyl groups, in a ratio by weight of 20:80 to 80:20 and preferably 40:60 to 60:40 or may be liposomally encapsulated in known manner. If liposomes are used, they may additionally contain vegetable proteins derived, for example, from soya or wheat incorporated in the membrane.

The following example further illustrates the practice of the invention, but is not intended to limit the scope of the invention.

EXAMPLE 1

Production Of An Unsaturated Fatty Acid Ethyl Ester By Transesterification

A mixture consisting of 20% by weight palm oil, 5% by weight rapeseed oil (from old plants), 50% by weight high-erucic rapeseed oil, 20% by weight sunflower oil and 5% by weight linseed oil was subjected to transesterification with ethanol in known manner. The resulting ethyl ester mixture showed the following fatty acid distribution:

| | |
|---|---|
| C12 | 0.07% by weight |
| C14 | 0.31% by weight |
| C16:0 | 14.64% by weight |
| C16:1 omega-7 | 0.15% by weight |
| C18:0 | 2.50% by weight |
| C18:1 omega-7 | 21.48% by weight |
| C18:2 omega-6 | 23.26% by weight |
| C18:3 omega-3 | 7.38% by weight |
| C20:0 | 0.52% by weight |
| C20:1 | 3.38% by weight |
| C22:1 | 21.71% by weight |

What is claimed is:

1. A method for providing a physiological nutrient to a cell culture, comprising adding esters of physiologically active fatty acids containing 16 to 24 carbon atoms and 2 to 5 double bonds to the cell culture, wherein said esters are esters of one or more sterols.

2. The method according to claim 1, wherein said one or more sterols are selected from the group consisting of β-sitosterol, campesterol, brassicasterol, avenasterol and stigmasterol.

3. The method according to claim 1, wherein said one or more sterols are selected from the group consisting of β-sitosterol, β-sitostanol and mixtures thereof.

4. The method of claim 1 wherein said physiologically active fatty acids comprise conjugated linoleic acid (CLA), omega fatty acids (OF) or mixtures thereof.

* * * * *